United States Patent
Bel-Rhlid et al.

(10) Patent No.: US 10,912,803 B2
(45) Date of Patent: Feb. 9, 2021

(54) PROBIOTIC AND POLYPHENOL AGAINST NEURODEGENERATION

(71) Applicant: NESTEC S.A., Vevey (CH)

(72) Inventors: Rachid Bel-Rhlid, Savigny (CH); Jane Durga, Miex (CH); Tina Kunz, Lausanne (CH); Jeroen Antonius Johannes Schmitt, Moudon (CH)

(73) Assignee: Societe des Produits Nestle S.A., Vevey (CH)

( * ) Notice: Subject to any disclaimer, the term of this patent is extended or adjusted under 35 U.S.C. 154(b) by 243 days.

(21) Appl. No.: 15/713,935

(22) Filed: Sep. 25, 2017

(65) Prior Publication Data

US 2018/0028582 A1    Feb. 1, 2018

Related U.S. Application Data

(63) Continuation of application No. 14/406,980, filed as application No. PCT/EP2013/062943 on Jun. 20, 2013, now Pat. No. 9,801,915.

(30) Foreign Application Priority Data

Jun. 22, 2012 (EP) .................................... 12173108

(51) Int. Cl.
| | |
|---|---|
| A61K 35/747 | (2015.01) |
| A23L 33/105 | (2016.01) |
| A61K 36/53 | (2006.01) |
| A23L 33/135 | (2016.01) |
| A61K 31/216 | (2006.01) |
| A61K 31/192 | (2006.01) |

(52) U.S. Cl.
CPC .......... *A61K 35/747* (2013.01); *A23L 33/105* (2016.08); *A23L 33/135* (2016.08); *A61K 31/192* (2013.01); *A61K 31/216* (2013.01); *A61K 36/53* (2013.01); *A23V 2002/00* (2013.01); *A23Y 2220/00* (2013.01); *A23Y 2220/43* (2013.01)

(58) Field of Classification Search
CPC ..... A61K 35/747; A61K 36/53; A23L 33/105; A23Y 2220/00
See application file for complete search history.

(56) References Cited

U.S. PATENT DOCUMENTS

| | | |
|---|---|---|
| 2012/0020926 A1 | 1/2012 | Bel-Rhlid et al. |
| 2012/0087902 A1 | 4/2012 | Rescigno et al. |

FOREIGN PATENT DOCUMENTS

| | | |
|---|---|---|
| EP | 1917960 | 5/2008 |
| WO | 2006138349 | 12/2006 |
| WO | 2007009187 | 1/2007 |
| WO | 2008055651 | 5/2008 |
| WO | 201008631 | 8/2010 |
| WO | 2010086322 | 8/2010 |
| WO | 2010086331 A2 | 8/2010 |
| WO | 2011083354 | 7/2011 |
| WO | 2012000957 A1 | 1/2012 |

OTHER PUBLICATIONS

Sinkovic et al. "Rosemary Extracts Improve Flow-mediated Dilation of the Brachial Artery and Plasma PAI-1 Activity in Healthy Young Volunteers." (2011), Phytotherapy Research, vol. 25: 402-407. (Year: 2011).*
Pengelly et al. "Short-Term Study on the Effects of Rosemary on Cognitive Function in an Elderly Population", 2012, J Medicinal Food, vol. 15(1): 10-17. (Year: 2012).*
Sul et al. "Protective effect of caffeic acid against beta-amyloid-induced neurotoxicity by the inhibition of calcium influx and tau phosphorylation", 2009, vol. 84, pp. 257-262.
Tsai et al. "Preventive and therapeutic effects of caffeic acid against inflammatory injury in stiatum of MPTP-treated mice " vol. pp. 441-447.
Yang et al. "Protection of Mouse Brain from Aluminum-induced Damag by Caffeic Acid" 2008, vol. 14, pp. 10-16.
Jeong et al. "Neuroprotective and anti-oxidant effects of caffeic acid isolated from Erigeron annus leaf", vol. 6 No. 25 pp. 1-9.
English Translation of Japanese Office Action dated May 30, 2017 for Patent Application No. P2015-517776.
Kalonia et al. "Effect of caffeic acid and rofecoxib and their combination against intrastriatal quinolinic acid unduced oxidative damage, mitochondrial and histological alterations in rats" (2009) Inflammopharacology, vol. 17:211-219.
Porat et al. "Inhibition of Amyloid Fibril Formation by Polyphenols: Structural Similarity and Aromatic Interactions as a Common Inhibition Mechanism" (2006) Chem Bol Drug Des, vol. 67:27-37.
Vauzour et al. "Caffeic acid, tyrosol and p-coumaric acid are potent inhibitors of 5-S-cysteinlynyl-dopamine induxed neurotoxity" (2010) Archives of Biochemistry and Biophysics, vol. 501: 106-111.
Wang et al. "Neurorescue Effect of Rosmarinic Acid on 6-Hydroxydopamine-Lesioned Nigral Dopamine Neurons in Rat Model of Parkinson's Disease" (2012) Journal of Molecular Neuroscience, vol. 113-119.
Ramassamy, "Emerging role of polyphenolic compounds in the treatment of neurodegenerative diseaseses: A review of their intracellular targets." (Sep. 2006), European Journal of Pharmacology: vol. 545, No. 1: 51-64.
Kelsey, "Nuracuetical Antioxidants as Novel Nuroprotective Agents" (2010), Molecules: vol. 15: 7792-7814.

\* cited by examiner

*Primary Examiner* — Teresa E Knight
(74) *Attorney, Agent, or Firm* — K&L Gates LLP

(57) ABSTRACT

A composition containing the probiotic strain *Lactobacillus johnsonii* CNCM 1-1225 in combination with a polyphenol for use in the treatment or prevention of a cognitive and/or neurodegenerative disorder, in particular Alzheimer's disease. The polyphenol can be one or more of rosmarinic acid, chicoric acid, or caftaric acid, and can be provided in the form of a plant extract.

14 Claims, 10 Drawing Sheets

PROBIOTIC AND POLYPHENOL AGAINST NEURODEGENERATION

PRIORITY CLAIM

This application is a continuation of U.S. application Ser. No. 14/406,980 filed Dec. 10, 2014, which is a National Stage of International Application No. PCT/EP13/062943 filed Jun. 20, 2013, which claims priority to European Patent Application No. 12173108.7 filed Jun. 22, 2012, the entire contents of which are incorporated herein by reference.

FIELD OF THE INVENTION

The present invention relates to a composition comprising the probiotic strain Lactobacillus johnsonii CNCM 1-1225 in combination with a polyphenol for use in the treatment or prevention of a cognitive and/or neurodegenerative disorder, in particular Alzheimer's disease.

In almost every country, the proportion of people aged over 60 years is growing faster than any other age group, which is at least in part due to a longer life expectancy. This population ageing can—consequently—be seen as a success story for the increase in health awareness as well as for the improved availability and performance of public health care. According to the WHO is the world's population of people that are older than 60 years presently 650 million. By 2050, the "greying" population is forecast to reach 2 billion.

Ageing, however, increases the risk to develop some diseases and it remains to be an aim of our society today to allow the population to age in good health. Central to the quality of life—in particular for the ageing population—is a proper cognitive performance and its maintenance.

Most common mental disorders affect cognitive functions, mainly memory processing, perception and problem solving. The most direct cognitive disorders are amnesia, dementia and delirium. Alzheimer's disease (AD) is the most common form of dementia. This presently incurable, degenerative, and terminal disease was first described by Alois Alzheimer in 1906. Generally Alzheimer is diagnosed in people over 65 years of age, although the less-prevalent early-onset Alzheimer's can occur much earlier. An estimated 26.6 million people worldwide had Alzheimer's in 2006; this number may quadruple by 2050.

Several age related disorders may be treated or prevented by a proper nutrition. However, with respect to cognitive disorders very little is known about nutritional measures one can undertake to prevent them. Therefore, identifying natural compounds that are active against amyloid plaque formation has been an object of science ever since amyloid plaque formation has been identified as a possible factor contributing to the progression of cognitive decline in Alzheimer's disease.

For example WO 2006/138349 discloses that natural compounds present in rosemary and sage exhibit potent anti-13A peptide activity. Furthermore, reservatrol from red wine, green tea catechins and the turmeric extract curcumin have received special attention for potential disease prevention or treatment of AD.

However, there is still a great need for finding new and better compositions that may be used to secure a proper cognitive function, and treat or prevent cognitive and/or neurodegenerative disorders.

Consequently, it was the object of the present invention to improve the state of the art and in particular to provide a composition that can be used to maintain cognitive function and to prevent cognitive and/or neurodegenerative disorders.

The inventors were surprised to see that they could achieve this object by the subject matter of the independent claim.

AD patients exhibit the formation of senile plaques. Senile plaques are extracellular deposits principally composed of insoluble aggregates of beta-amyloid (βA). These plaques or βA fibril deposits are believed to be responsible for the pathology of a number of neurodegenerative diseases including, but not limited to, Alzheimer's disease. They are also involved in cerebral amyloid angiopathy, neuronal loss, and cerebral atrophy leading to dementia. All these disorders can be treated and/or prevented by the use of the present invention.

The inventors have performed two different assays to test molecules for their ability to target different states along the amyloid formation pathway of Aβ42. The inventors found that the probiotic strain Lactobacillus johnsonii CNCM 1-1225 (Lal) in combination with a polyphenol was able to prevent and/or inhibit of Aβ oligomerization and/or fibrillogenesis in a synergistic way, and have hence identified Lactobacillus johnsonii CNCM 1-1225 (Lal) in combination with a polyphenol as a food-grade composition that can inhibit, retard and/or reverse, e.g., AD associated neuropathology, memory loss and/or cognitive decline.

DETAILED DESCRIPTION

Figure 1:
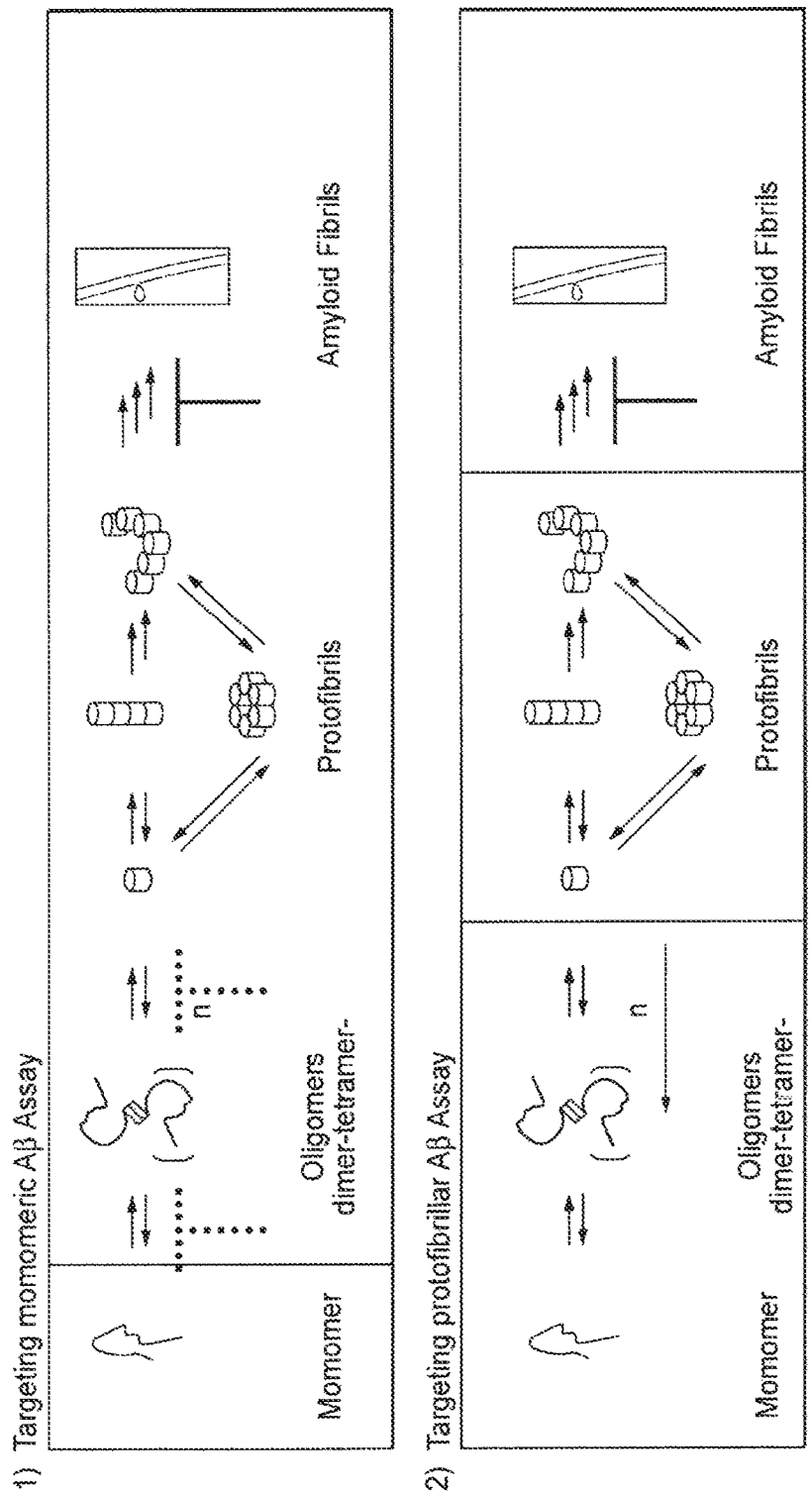
FIG. 1 shows a schematic representation of the assays performed.
Figure 2A:
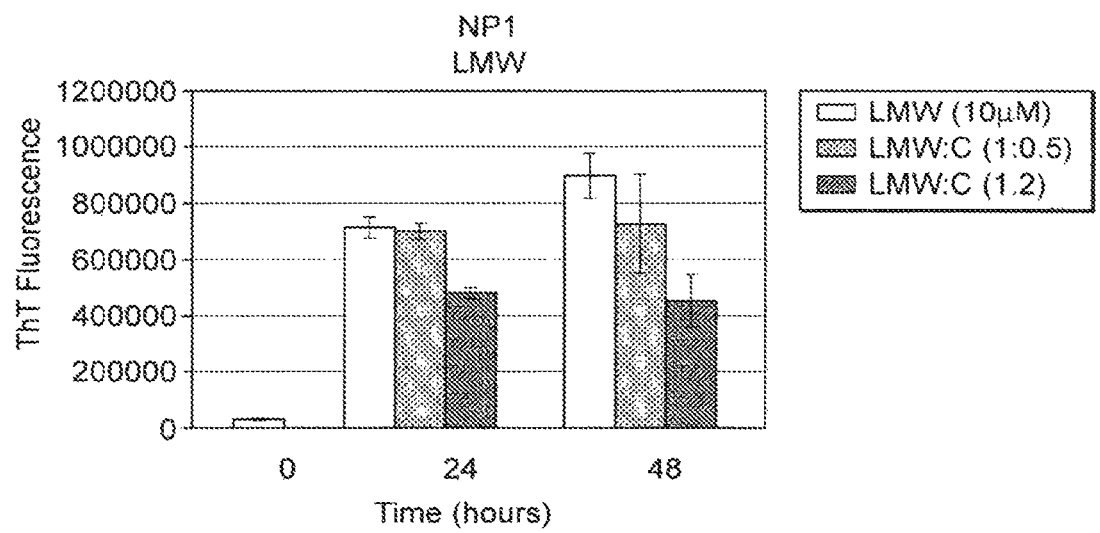
FIGS. 2A-2D show the results of the ThT Fluorescence measurements in Assay 1 (LMW) and in Assay 2 (PF). Tested were commercially available rosemary extract (NP1) and commercially available rosemary extract in combination with Lactobacillus johnsonii CNCM 1-1225 (Lal) (NP2). Clearly, Lal is able to potentiate the effect of rosemary extract.
Figure 2B:
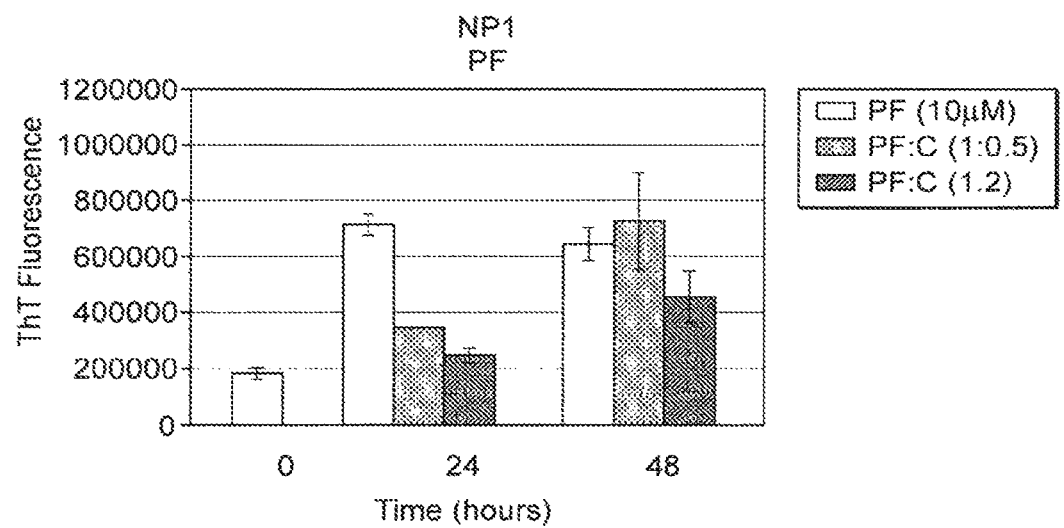
Figure 2C:
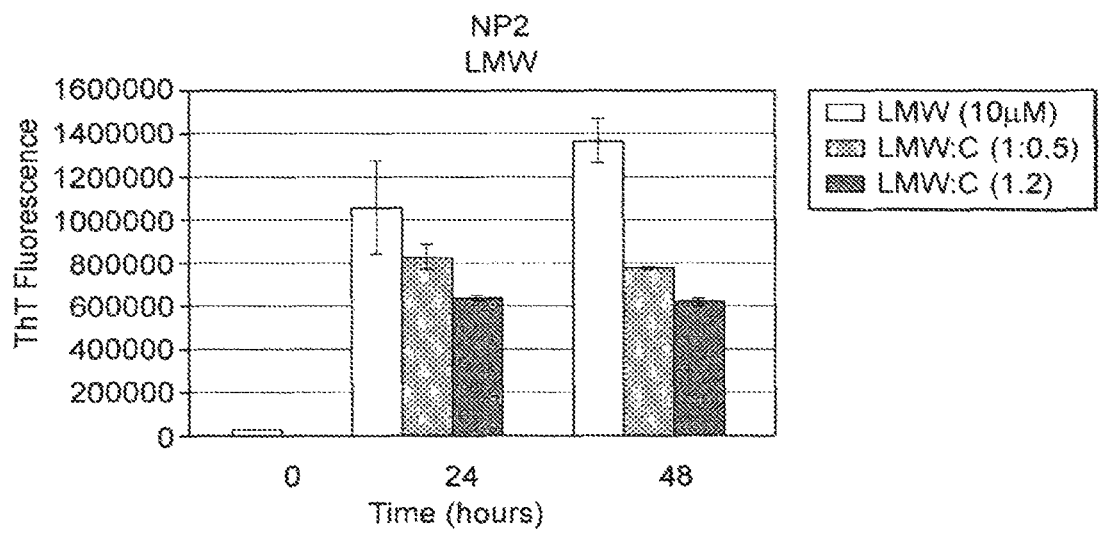
Figure 2D:
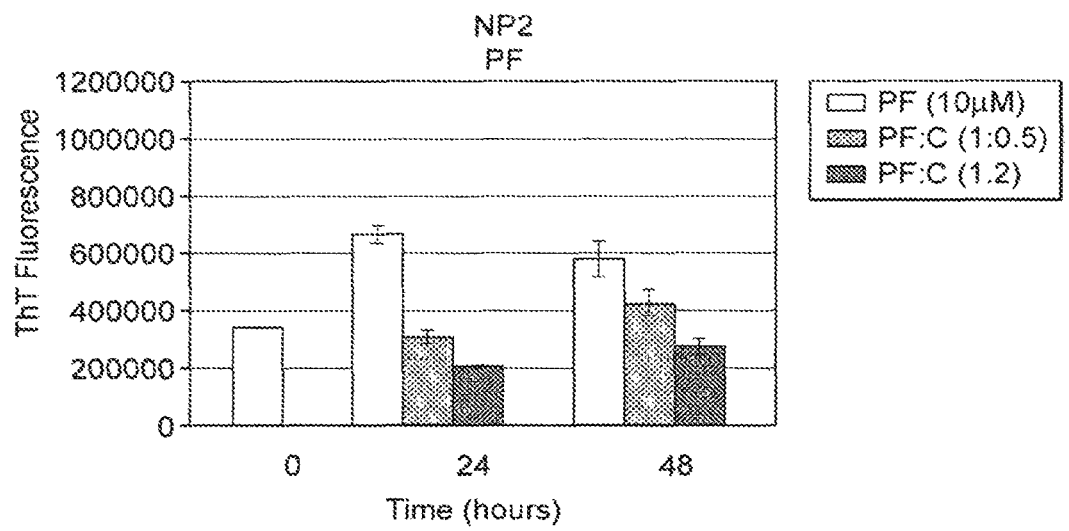
Figure 3A:
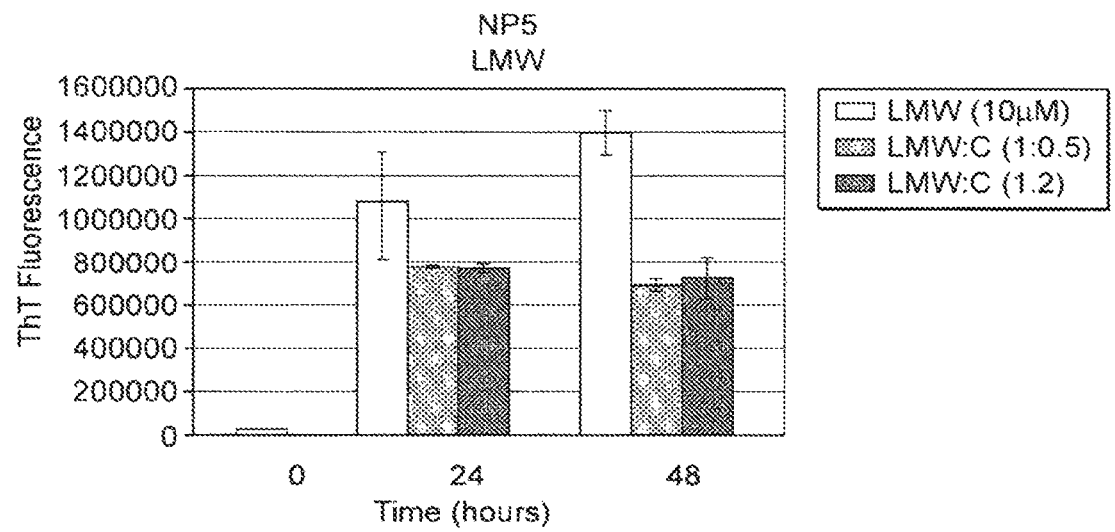
FIGS. 3A-3D show the results of the ThT Fluorescence measurements in Assay 1 (LMW) and in Assay 2 (PF). Tested were chicoric acid (NP5) and chicoric acid in combination with Lal (NP6). Clearly, Lal is able to potentiate the effect of chicoric acid.
Figure 3B:
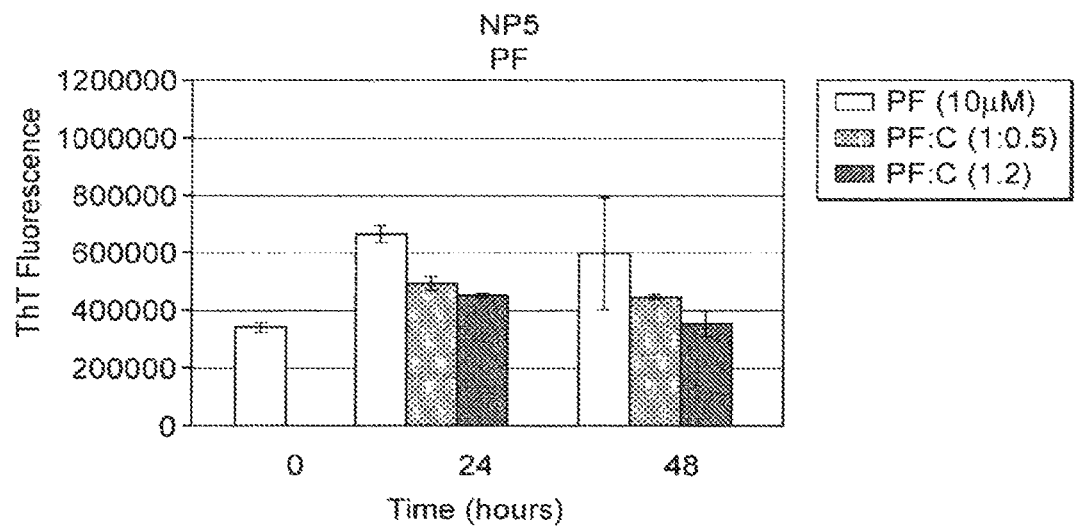
Figure 3C:
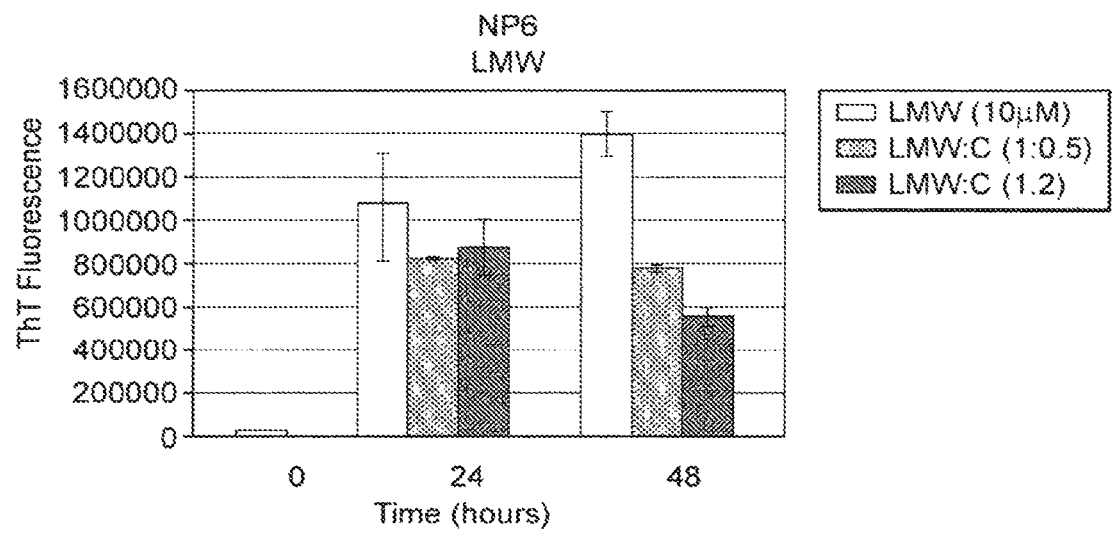
Figure 3D:
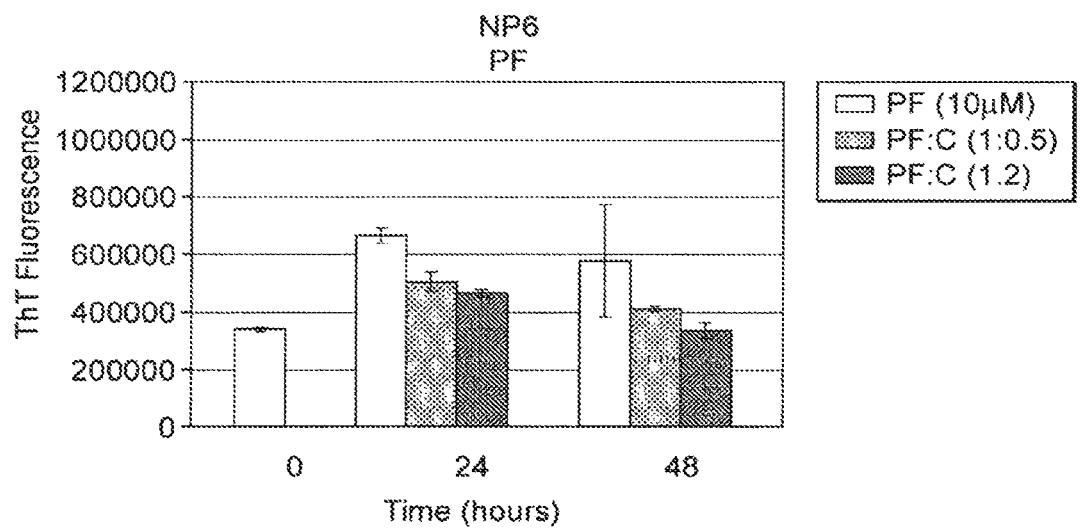
Figure 4A:
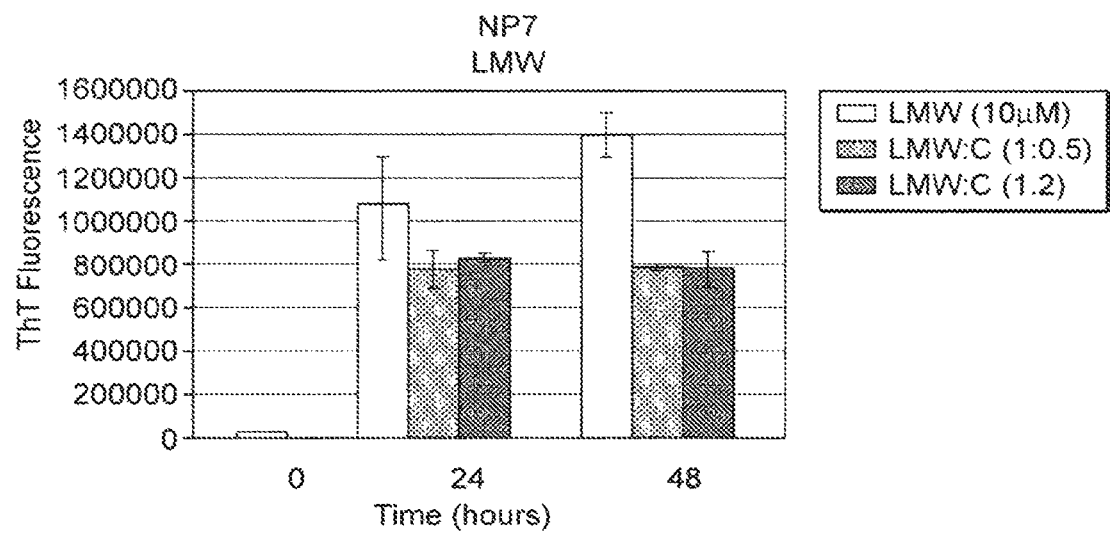
FIGS. 4A-4D shows the results of the ThT Fluorescence measurements in Assay 1 (LMW) and in Assay 2 (PF). Tested were caftaric acid (NP7) and caftaric acid in combination with Lal (MP8). Clearly, Lal able to potentiate the effect of caftaric acid.
Figure 4B:
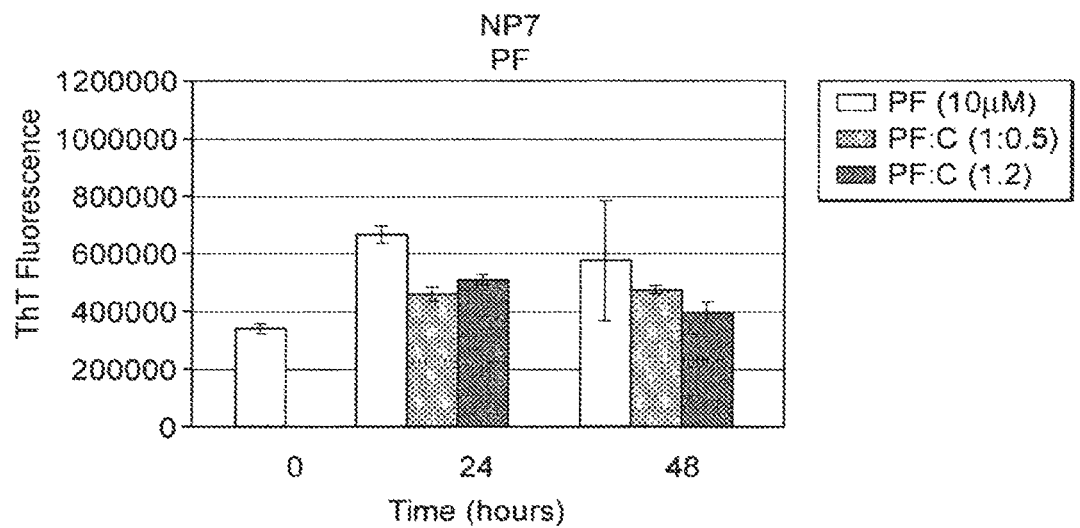
Figure 4C:
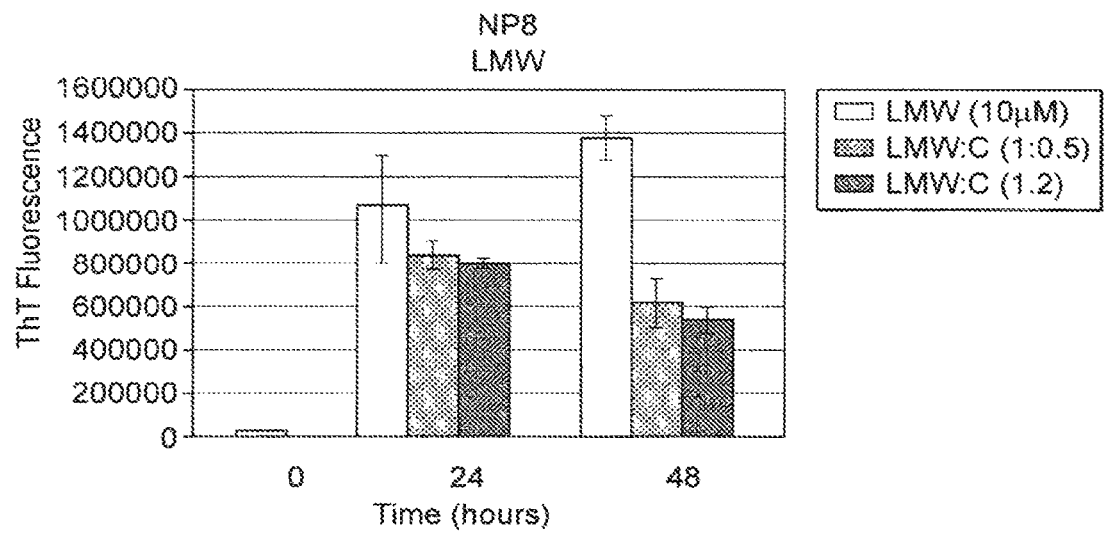
Figure 4D:
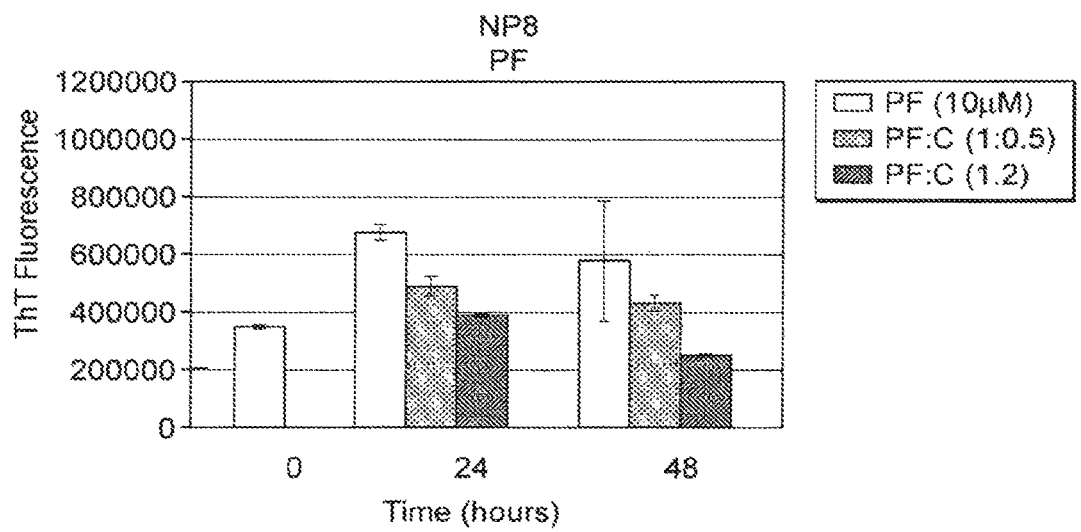
Figure 5A:
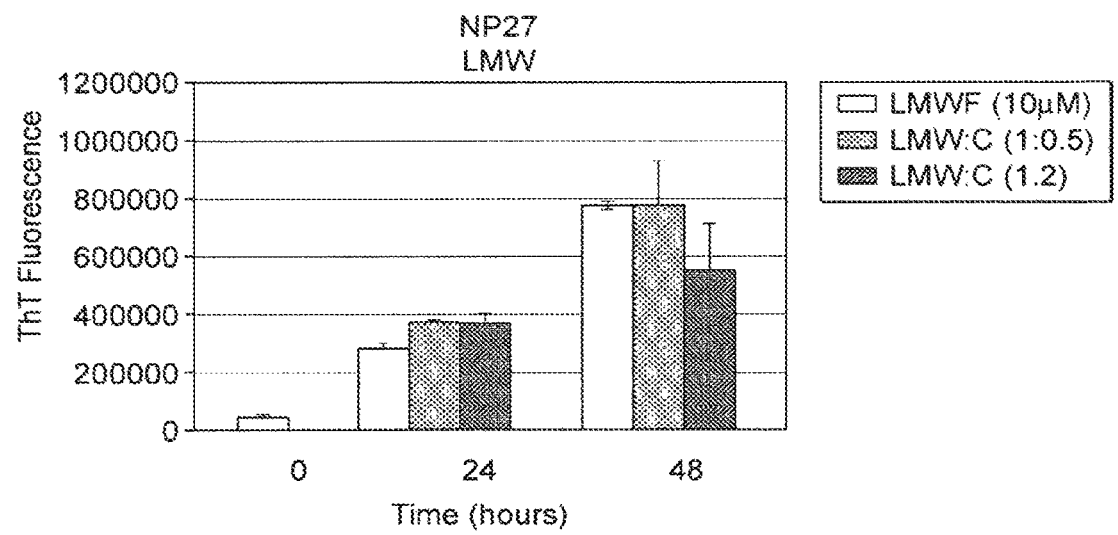
FIGS. 5A-5F show the results of the ThT Fluorescence measurements in Assay 1 (LMW) and in Assay 2 (PF). Tested was Lal in different concentrations. By itself, Lal does not show an effect.
Figure 5B:
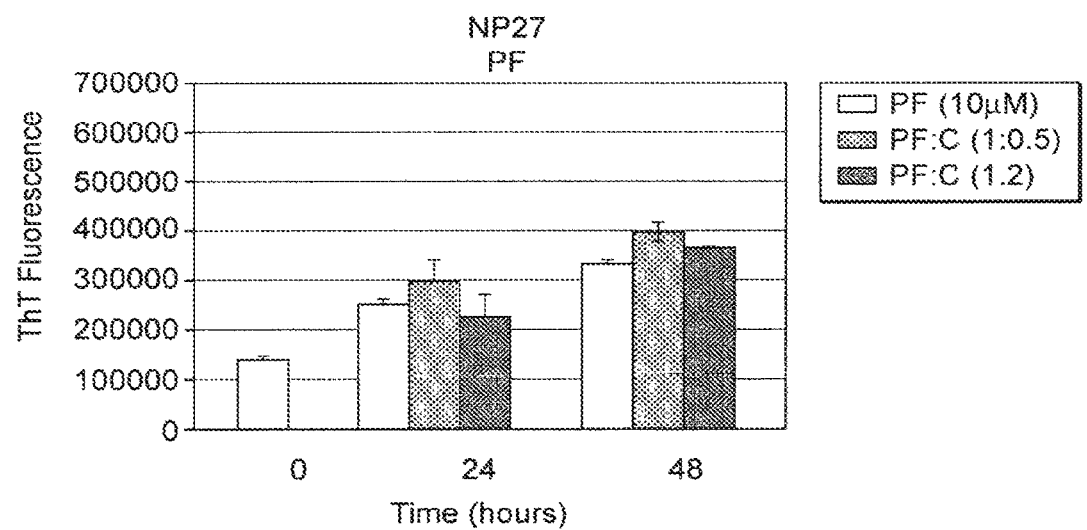
Figure 5C:
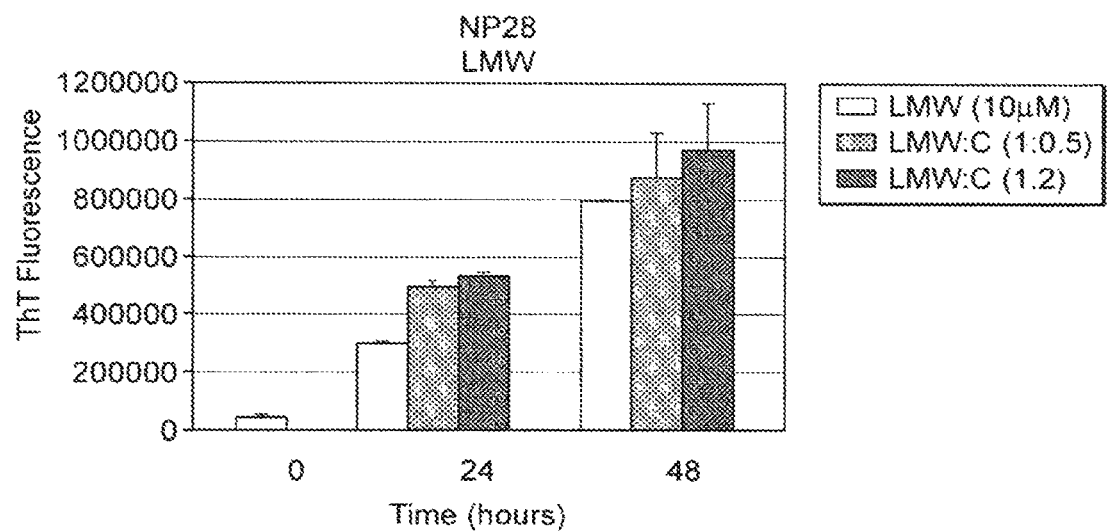
Figure 5D:
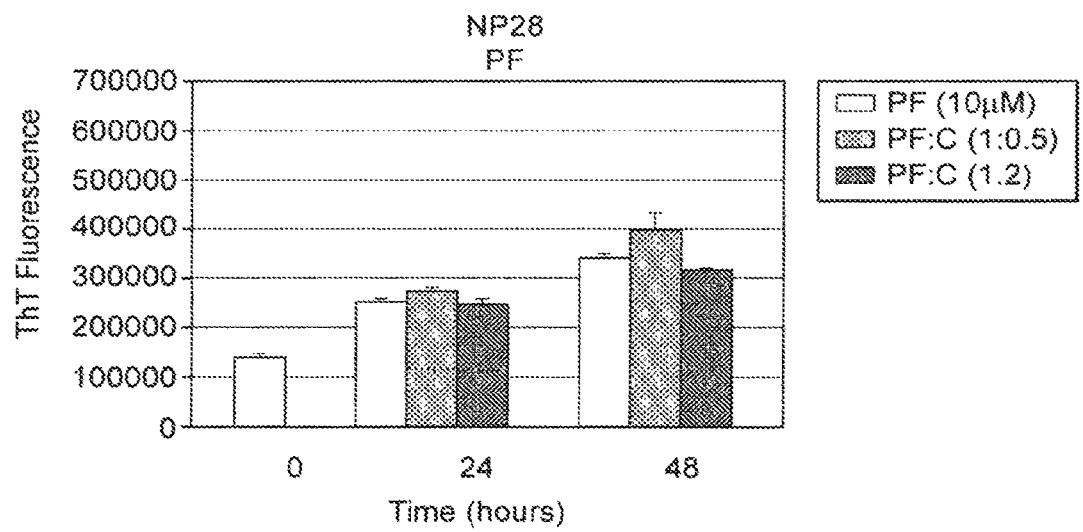
Figure 5E:
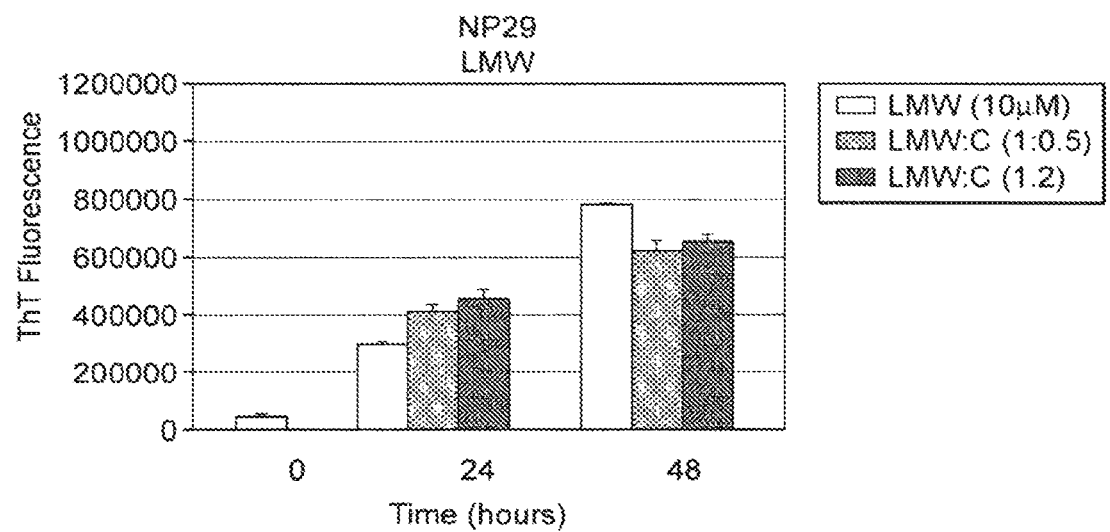
Figure 5F:
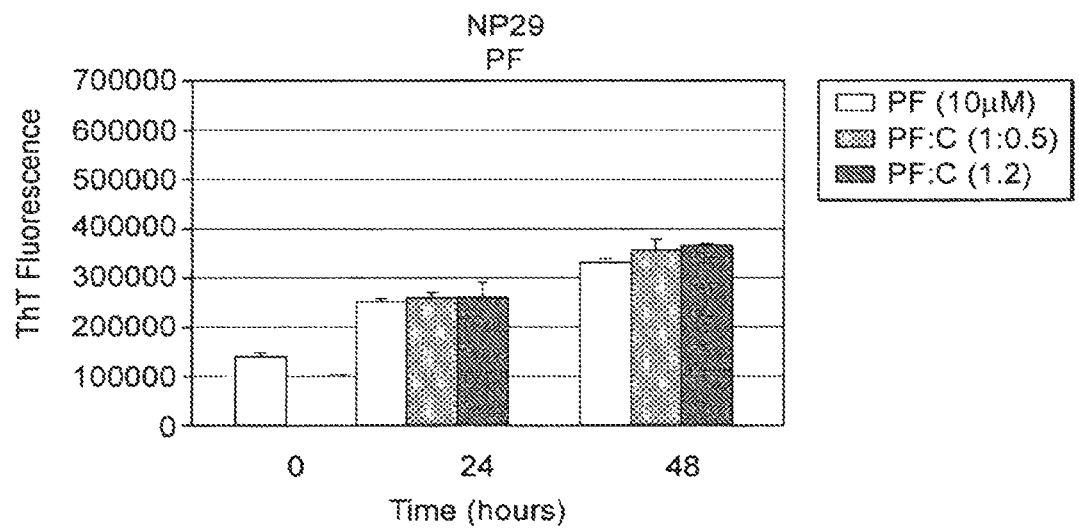

The present invention provides a composition comprising Lactobacillus johnsonii CNCM 1-1225 in combination with a polyphenol for use in the treatment or prevention of a cognitive and/or neurodegenerative disorder, and particularly where the disorder is linked to protein aggregation in the brain.

The inventors have found that probiotics, e.g., Lactobacillus johnsonii CNCM 1-1225 (Lal), may be used to treat or prevent all disorders that are linked to protein aggregation, such as amyloid plaque formation, for example. A list of disorders that are linked to protein aggregation was published by Selkoe D J., Nature. 2003 Dec. 18; 426(6968): 900-4. Review. Erratum in: Nature. 2004 Mar. 25; 428 (6981):445.

Disorders linked to protein aggregation include the following: Systemic extracellular amyloidoses, such as primary systemic amyloidosis, secondary systemic amyloidosis, familial Mediterranean fever, familial amyloidotic polyneuropathy 1, senile systemic amyloidosis, familial amyloidotic polyneuropathy 2, haemodialysis-related amyloidosis, Finnish hereditary amyloidosis, lysozyme amyloidosis, insulin-related amyloid, and/or fibrinogen a-chain amyloidosis;

Organ-limited extracellular amyloidoses, such as Alzheimer's disease, spongiform encephalopathies, hereditary cerebral haemorrhage with amyloidosis, type II diabetes, medullary carcinoma of the thyroid, and/or atrial amyloidoses;

Human brain diseases characterized by progressive misfolding and aggregation of proteins, such as Alzheimer's disease, frontotemporal dementia with Lewy bodies, Creutzfeldt-Jakob disease, polyglutamine expansion diseases (e.g., Huntington's disease spinocerebellar ataxias), and/or amyotrophic lateral sclerosis.

For example, the cognitive disorder that may be treated or prevented by the use of the present invention may be selected from the group consisting of neurodegenerative disorders, cognitive decline and combinations thereof. Typical neurodegenerative disorders are in this respect Alzheimer's disease, Creutzfeldt-Jakob disease, Huntington's disease and Parkinson's disease.

Additionally, disorders that are commonly seen with AD, demential and/or cognitive impairment may be treated with the use of the present invention. Such disorders include, for example sleep disorders, mood disorders and/or depression The polyphenol may be selected from the group consisting of 4"-(3'"-methoxy-4'"-hydroxyphenyl)-2"-oxo-3"-enebutanyl 3-(3'-methoxy-4'hydroxyphenyl)propenoate (calebin-A), 1,7-bis(4-hydroxy-3-methoxyphenyl)-1,4,6-heptatrien-3-one, 1,7-bis(4-hydroxy-3-methoxyphenyl)-1,6-heptadiene-3,5-dione (curcumin), 1-(4-hydroxy-3-methoxyphenyl)-7-(4-hydroxyphenyl)-1,6-heptadiene-3,5-dione (demethoxycurcumin), 1,7-bis(4-hydroxyphenyl)-1,6-heptadiene-3,5-dione (bisdemethoxycurcumin), 1-hydroxy-1,7-bis(4-hydroxy-3-methoxyphenyl)-6-heptene-3,5-dione, 1,7-bis(4-hydroxyphenyl)-1-heptene-3,5-dione, 1,7-bis(4-hydroxyphenyl)-1,4,6-heptatrien-3-one, 1,5-bis(4-hydroxy-3-methoxyphenyl)-1,4-pentadien-3-one, 2-shogaol, 4-shogaol, 6-shogaol, 8-shogaol, 2-gingerol, 4-gingerol, 6-gingerol, 8-gingerol, ginkgolic acids, rosmanol, isorosmanol, rosmadial, carnosol, carnosic acid, epirosmanol, rosmarinic acid, caftaric acid, chicoric acid, reservatrol, and/or catechins.

In a preferred embodiment of the present invention, however, the polyphenol is selected from the group consisting of rosmarinic acid, caftaric acid and chicoric acid, or combinations thereof.

Since these polyphenols are all naturally occurring compounds in plants, they may be provided for example as plants or in the form of plant extracts. Typical plants that may be used to provide the polyphenols may be for example *Curcuma* sp., *Zingiber* sp., *Ginkgo biloba, Salvia* sp., *Romarinus* sp., or combinations thereof.

In one preferred embodiment, the rosmarinic acid is provided in the form of a rosemary extract.

In an alternative embodiment, the polyphenol is provided in the form of a pharmaceutically accepted salt.

The *Lactobacillus johnsonii* strain Lal was deposited by Nestec S. A. according to the Budapest Treaty with the Collection Nationale de Cultures de Microorganismes (CNCM), Institut Pasteur, 28 rue du Docteur Roux, F-75724 Paris Cedex 15, France, on Jun. 30, 1992, where it was attributed the deposit number CNCM 1-1225. The strain is described in EP 0577904 and has in the meantime been reclassified as *Lactobacillus johnsonii* due to changes in the bacterial taxonomy.

The present invention pertains to the composition, wherein the *Lactobacillus johnsonii* CNCM 1-1225 is in the form of viable bacteria, non-replicating bacteria and/or as medium or fraction of the medium the bacteria was cultivated in. Hence, in one embodiment of the present invention, the probiotics are used as living micro-organisms. In another embodiment of the present invention, the probiotics are used as non-replicating micro-organisms. For example, at least 95% of the probiotics present in a composition may be non-replicating. In a still further embodiment of the present invention, the probiotics are provided as an extract of a medium that contains at least a part of the metabolites produced by the *Lactobacillus johnsonii* that were cultivated in that medium. The *Lactobacillus johnsonii* themselves may then be removed before the composition is administered. Hence, if the *Lactobacillus johnsonii* are to be used together with polyphenols, the polyphenols may be combined with the lactobacilli in a medium that allows the lactobacilli to be metabolically active. The *Lactobacillus johnsonii* may then be removed from the medium when the composition described in the present invention is prepared.

In therapeutic applications, compositions are administered in an amount sufficient to at least partially cure or arrest the symptoms of the disorder and/or its complications. An amount adequate to accomplish this is defined as "a therapeutically effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

Consequently, the *Lactobacillus johnsonii* CNCM 1-1225 is administered in a therapeutically effective dose and/or in a prophylactic effective dose. Typically, the *Lactobacillus johnsonii* CNCM 1-1225 may be present in the composition in an amount equivalent to between $10^2$ and $10^{11}$ cfu/g dry mass of the composition. This expression includes the possibilities that the bacteria are live, inactivated or dead or even present as fragments such as DNA or cell wall materials. In other words, the quantity of bacteria which the composition contains is expressed in terms of the colony forming ability of that quantity of bacteria as if all the bacteria were live irrespective of whether they are, in fact, live, inactivated or dead, fragmented or a mixture of any or all of these states. Preferably the *Lactobacillus johnsonii* CNCM 1-1225 is present in an amount equivalent to between $10^3$ and $10^9$ cfu/g dry mass of the composition, even more preferably in an amount equivalent to between $10^4$ and $10^8$ cfu/g of dry composition.

Likewise, the polyphenol is administered in a therapeutically effective dose and/or in a prophylactic effective dose. Typically, a polyphenol is present in the composition in an amount in the range of 1-100 mg/g dry mass of the composition.

In a further embodiment, the *Lactobacillus johnsonii* CNCM I-1225 is encapsulated. In a still further embodiment the *Lactobacillus johnsonii* CNCM 1-1225 in combination with the polyphenol is encapsulated. Encapsulation technology is well known in the art and could be applied here to either the *Lactobacillus johnsonii* itself or to the composition of the invention as a whole. Condition is that the encapsulation releases its enclosed substances once ingested by a patient or subject in need thereof.

The composition described in the present invention may be administered to pets and to farm animals such as e.g. cows to protect them against the development of amyloid plaque related disorders, such as the Creutzfeldt-Jakob disease.

In another embodiment, the composition is to be administered to humans. Humans at risk for developing the symptoms of amyloid plaque related disorders are typically older than 60 years. Hence in one embodiment of the present invention, the composition is to be administered to humans that are older than 60. However, considering the fact that the composition described in the present invention may also be used to prevent cognitive disorders and considering further that it is meanwhile known that the amyloid plaque formation may begin a long time before the first symptoms of an amyloid plaque related disease become apparent, it is a more preferred embodiment of the present invention that the composition is to be administered to humans that are older than 50, even more preferred older than 40.

The composition described in the present invention may be in the form of a food product, an animal food product, a pharmaceutical composition, a nutritional formulation, a nutraceutical, a beverage, a food supplement or a food additive. Hence, it may for example further comprise a source of protein, a source of lipids, and/or a source of carbohydrate. For example, if the composition is a nutritional formula, it may comprise all three macro-nutrients. Preferably the composition is in a form suitable for oral or enteral administration.

If the composition is provided in a dry form, for example as a powder, it may be desired to provide the composition in a form that allows longer storage times. It was found that shelf stability can be obtained, for example by providing the composition with a water activity smaller than 0.2, for example in the range of 0.19-0.05, preferably smaller than 0.15. Such a low water activity will for example allow that living *lactobacillus* micro-organism will remain viable for longer time periods. Water activity or aw is a measurement of the energy status of the water in a system. It is defined as the vapor pressure of water divided by that of pure water at the same temperature; therefore, pure distilled water has a water activity of exactly one.

The composition of the invention may also further comprise at least one prebiotic, for example in an amount of from 0.3 to 10 wt %. "Prebiotic" means food substances that promote the growth of probiotics in the intestines. They are not broken down in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®.

Those skilled in the art will understand that they can freely combine all features of the present invention disclosed herein. Further advantages and features of the present invention are apparent from the figures and examples.

Example 1

The goal of this study was to identify biologically active components that could inhibit, retard and/or reverse AD associated neuropathology, memory loss and cognitive decline. Towards achieving this goal, bioactive compounds were identified that can perturb the individual steps on the amyloid cascade implicated, e.g., in the pathogenesis of Alzheimer's disease.

More specifically, compounds were identified that can be used for the prevention and/or inhibition of Aβ oligomerization and/or fibrillogenesis. Two different assays were performed.

Assay 1: Targeting Monomeric Aβ Assay (Timeframe 24-48 Hrs) (See FIG. 1):

In this assay, it was started with size exclusion purified monomeric Aβ42 (LMW). This was incubated with a compound of interest (C) at 37° C. The extent of aggregation was then assessed at 24 and 48 hrs by Thioflavin T (ThT) fluorescence. ThT is a hydrophobic dye that exhibits enhanced fluorescence upon binding to amyloid fibrils. ThT binds specifically to amyloid fibrils, but not monomeric forms of A. In this assay a decrease or absence of ThT fluorescence indicates that the molecule being tested reduces and/or blocks the formation of amyloid fibrils. However, it is difficult to infer from this assay alone at which point along the amyloid formation pathway the compound acts, i.e., does interfere with monomer to protofibrils transition or block protofibrils to fibril transition.

Assay 2: Targeting Protofibrillar Aβ Assay (Timeframe 24-48 Hrs) (See FIGS. 1 and 2A-2D):

In this assay it was started with a size exclusion purified protofibrillar mixture of Aβ42 (PF). This was incubated with the compound of interest (C) at 37° C. The extent of aggregation was then assessed at 24 and 48 hrs by Thioflavin T (ThT) fluorescence. A decrease or absence of an increase in ThT fluorescence signal of protofibrils indicates that the molecule being tested reduces and/or blocks the formation of amyloid fibrils. This could occur via at least two mechanisms; i) blocking protofibrils to fibril transition or ii) inducing the dissociation/disaggregation of protofibrils. A decrease in the ThT signal of protofibrils would suggest that dissociation of protofibrils is taking place, whereas an unchanged ThT signal would suggest inhibition of fibril formation by stabilization of protofibrils.

Aβ42 LMW and PF were used at a final concentration of 10 pM and incubated alone or with the compounds at a ratio of 1:0.5 or 1:2.

The following compounds were tested:
NP1: Rosemary extract
NP2: Rosemary extract+Lal
NP5: Chicoric acid
NP6: Chicoric acid+Lal
NP7: Caftaric acid
NP8: Caftaric acid+Lal
NP27: Lal 10 mg/ml
NP28: Lal 90 mg/ml
NP29: Lal 60 mg/ml They were prepared as follows:

NP1: 10 mg of Rosemary extract (Robertet P31) from Robertet (France) was dissolved in 1 ml phosphate buffer (10 mM, pH 7.0) and the mixture was incubated 6 h at 37° C. (thermomixer)

NP2: 10 mg of Rosemary extract (Robertet P31) from Robertet (France) was dissolved in 1 ml phosphate buffer (10 mM, pH 7.0). To this solution, 10 mg of a spray-dried preparation of Lal was added and the mixture was incubated 6 h at 37° C. (thermomixer). The cells were removed by centrifugation (3000 g, 5 min) and the supernatant tested.

NP5: Chicoric acid (10 mM, produced internally by organic synthesis) in phosphate buffer (pH 7.0) was incubated 24 h at 37° C.

NP6: To chicoric acid (10 mM, produced internally by organic synthesis) in phosphate buffer (pH 7.0), 60 mg of a spray-dried preparation of Lal was added. The mixture was then incubated 24 h at 37° C. (thermomixer). The cells were removed by centrifugation (3000 g, 5 min) and the supernatant tested.

NP7: Caftaric acid (10 mM, produced internally by organic synthesis) in phosphate buffer (pH 7.0) was incubated 24 h at 37° C.

NP8: To caftaric acid (10 mM, produced internally by organic synthesis) in phosphate buffer (pH 7.0), 90 mg of a spray-dried preparation of Lal was added. The mixture was then incubated 24 h at 37° C. (thermomixer). The cells were removed by centrifugation (3000 g, 5 min) and the supernatant tested. NP27, NP28 and NP29: A 10 mg, 90 mg or 60 mg of a spray-dried preparation of Lal was dissolved in 1 ml phosphate butter (10 mM, pH 7.0) and incubated 24 h at 37° C. (thermomixer). The cells were removed by centrifugation (3000 g, 5 min) and the supernatant tested.

The results are shown in FIGS. 2A-2D, 3A-3D, 4A-4D and 5A-5F, and in Table 1 and 2.

TABLE 1

| | NP1 (1:0.5) | NP2 (1:0.5) | NP1 (1:2) | NP2 (1:2) |
|---|---|---|---|---|
| LMW (effects of compounds compared to control without compounds) - signal intensity | | | | |
| 24 h | No effect | Slight decrease (stronger effect than with NP1) | Decrease | Decrease (stronger effect than with NP1) |
| 48 h | Decrease | Decrease (stronger effect than with NP1) | Decrease | Decrease (stronger effect than with NP1) |
| PF (effects of compounds compared to control without compounds) - signal intensity | | | | |
| 24 h | Slight decrease | Decrease (stronger effect than with NP1) | Decrease | Decrease (stronger effect than with NP1) |
| 48 h | Decrease | Decrease (same effect as with NP1) | Decrease | Decrease (same effect as with NP1) |

NP1: Rosemary extract
NP2: Rosemary extract + Lal

| | NP5 (1:0.5) | NP6 (1:0.5) | NP5 (1:2) | NP6 (1:2) |
|---|---|---|---|---|
| LMW (effects of compounds compared to control without compounds) - signal intensity | | | | |
| 24 h | Decrease | Decrease (same effect as with NP5) | Decrease | Decrease (same effect as with NP5) |
| 48 h | Decrease | Decrease (same effect as with NP5) | Decrease | Decrease (stronger effect than with NP5) |
| PF (effects of compounds compared to control without compounds) - signal intensity | | | | |
| 24 h | Decrease | Decrease (same effect as with NP5) | Decrease | Decrease (same effect as with NP5) |
| 48 h | Decrease | Decrease (same effect as with NP5) | Decrease | Decrease (same effect as with NP5) |

NP5: Chicoric acid
NP6: Chicoric acid + Lal

| | NP7 (1:0.5) | NP8 (1:0.5) | NP7 (1:2) | NP8 (1:2) |
|---|---|---|---|---|
| LMW (effects of compounds compared to control without compounds) - signal intensity | | | | |
| 24 h | Decrease | Decrease (same effect as with NP7) | Decrease | Decrease (same effect as with NP7) |
| 48 h | Decrease | Decrease (stronger effect than with NP7) | Decrease | Decrease (stronger effect than with NP7) |
| PF (effects of compounds compared to control without compounds) - signal intensity | | | | |
| 24 h | Decrease | Decrease (same effect as with NP7) | Decrease | Decrease (stronger effect than with NP7) |
| 48 h | Decrease | Decrease (same effect as with NP7) | Decrease | Decrease (stronger effect than with NP7) |

NP7: Cafteric acid
NP8: Cafteric acid + Lal

TABLE 2

| | Inhibition of Aβ fibrillization | | |
|---|---|---|---|
| NP 1 | LMW | 50% | |
| | PF | 62% | |
| NP 2 | LMW | 57% | |
| | PF | 58% | |
| NP 5 | LMW | 50% | |
| | PF | 41% | |
| NP 6 | LMW | 60% | |
| | PF | 41% | |
| NP 7 | LMW | 42% | |
| | PF | 35% | |
| NP 8 | LMW | 60% | |
| | PF | 58% | |
| NP 27 | LMW | 27% | |
| | PF | 0% | no activity |
| NP 28 | LMW | 0% | |
| | PF | 5% | no activity |
| NP 29 | LMW | 18% | |
| | PF | 0% | no activity |

The invention is claimed as follows:

1. A method of treating Alzheimer's disease in an individual in need thereof, the method comprising the step of administering to the individual a composition comprising *Lactobacillus johnsonii* CNCM I-1225 in combination with rosmarinic acid in an amount effective to prevent and/or inhibit Aβ oligomerization and/or fibrillogenesis to an individual in need of same.

2. The method according to claim 1, wherein the rosmarinic acid is provided in the form of a rosemary extract.

3. The method according to claim 1, wherein the rosmarinic acid is provided in the form of a pharmaceutically accepted salt.

4. The method according to claim 1, wherein the *Lactobacillus johnsonii* CNCM I-1225 is in the form of viable bacteria or non-replicating bacteria.

5. The method according to claim 1, wherein the composition comprises the *Lactobacillus johnsonii* CNCM I-1225 in an amount of between $10^2$ and $10^{11}$ cfu/g dry mass of the composition.

6. The method according to claim 1, wherein the *Lactobacillus johnsonii* CNCM I-1225 is encapsulated.

7. The method according to claim 1, wherein the individual in need of same is a human or pet.

8. The method according to claim 1, wherein the composition is selected from the group consisting of food products, animal food products, pharmaceutical compositions, nutritional formulations, nutraceuticals, beverages, food supplements, and food additives.

9. The method according to claim 1, wherein the composition has a water activity of less than 0.2.

10. The method according to claim 1, wherein the composition comprises an additional ingredient selected from the group consisting of a source of protein, a source of lipids, a source of carbohydrate, and combinations thereof.

11. The method according to claim 1, wherein the individual in need of same is a human older than 40.

12. A method of treating Alzheimer's disease in an individual in need thereof, the method comprising administering to the individual a composition comprising *Lactobacillus johnsonii* CNCM1-1225 in combination with rosmarinic acid in the form of a rosemary extract in an amount effective to prevent and/or inhibit A[3 oligomerization and/or fibrillogenesisto an individual in need of same, wherein the *Lactobacillus johnsonii* CNCM 1-1225 comprises $10^2$ to $10^{11}$ cfu/g dry mass of the composition.

13. The method according to claim 12, wherein the composition comprises an additional ingredient selected from the group consisting of a source of protein, a source of lipids, a source of carbohydrate, and combinations thereof.

14. The method according to claim 12, wherein the individual in need of same is a human older than 40 years.

* * * * *